US010458934B2

(12) United States Patent
Bild et al.

(10) Patent No.: US 10,458,934 B2
(45) Date of Patent: Oct. 29, 2019

(54) TOOL FOR CUTOFF VALUE DETERMINATION IN NET-PAY COMPUTATION WORKFLOW

(71) Applicant: SCHLUMBERGER TECHNOLOGY CORPORATION, Sugar Land, TX (US)

(72) Inventors: Claire Bild, Clamart (FR); Sylvain Wlodarczyk, Montpellier (FR); Florent D'Halluin, Clamart (FR); Jean-Etienne Jacolin, Montpellier (FR)

(73) Assignee: Schlumberger Technology Corporation, Sugar Land, TX (US)

(*) Notice: Subject to any disclaimer, the term of this patent is extended or adjusted under 35 U.S.C. 154(b) by 427 days.

(21) Appl. No.: 15/500,499

(22) PCT Filed: Jul. 29, 2015

(86) PCT No.: PCT/US2015/042572
§ 371 (c)(1),
(2) Date: Jan. 30, 2017

(87) PCT Pub. No.: WO2016/018973
PCT Pub. Date: Feb. 4, 2016

(65) Prior Publication Data
US 2017/0212064 A1    Jul. 27, 2017

(30) Foreign Application Priority Data

Jul. 29, 2014    (FR) ...................................... 14 57311

(51) Int. Cl.
*G01N 24/08*    (2006.01)
*G01N 33/24*    (2006.01)
(Continued)

(52) U.S. Cl.
CPC .......... *G01N 24/081* (2013.01); *E21B 43/16* (2013.01); *E21B 49/00* (2013.01); *G01N 33/241* (2013.01);
(Continued)

(58) Field of Classification Search
CPC .. G01N 24/081; G01N 33/241; G01N 33/246; E21B 43/16; E21B 49/00;
(Continued)

(56) References Cited

U.S. PATENT DOCUMENTS 8,311,789 B2* 11/2012 Eyvazzadeh ............ E21B 47/00
703/10
2003/0144796 A1    7/2003 Anstey et al.
(Continued)

FOREIGN PATENT DOCUMENTS

CN    103698811 A    4/2014
WO    2014/055810 A1    4/2014

OTHER PUBLICATIONS

Crain, "Crain's Petrophysical Handbook—Water Saturation Crossplots," Nov. 14, 2009, pp. 1-8.*
(Continued)

*Primary Examiner* — Manuel L Barbee

(57) ABSTRACT

Methods, systems, and computer-readable media for assessing porosity and water saturation cutoff values for hydrocarbon volume estimation are described. The techniques can include determining a plurality of water saturation and porosity value pairs for locations regularly-spaced along at least one borehole. The techniques can further include plotting the plurality of water saturation and porosity value pairs on a graph and representing a plurality of percentiles of the estimated maximal hydrocarbon volume on the graph. The techniques can also include causing the graph to be displayed to a user, such that the user can visually observe
(Continued)

a combined sensitivity to porosity and water saturation cutoffs values. The user can take various actions based on the display.

20 Claims, 6 Drawing Sheets

(51) Int. Cl.
 *E21B 43/16* (2006.01)
 *E21B 49/00* (2006.01)
 *G01V 1/50* (2006.01)
 *G01V 3/32* (2006.01)
 *G01V 9/02* (2006.01)
(52) U.S. Cl.
 CPC ............. *G01N 33/246* (2013.01); *G01V 1/50* (2013.01); *G01V 3/32* (2013.01); *G01V 9/02* (2013.01); *G01V 2210/6244* (2013.01)
(58) Field of Classification Search
 CPC ... G01V 1/50; G01V 3/32; G01V 9/02; G01V 2210/6244
 See application file for complete search history.

(56) References Cited

U.S. PATENT DOCUMENTS

2013/0265043 A1* 10/2013 Nicot ................... G01N 24/081
 324/303
2014/0207383 A1 7/2014 Embid Droz et al.

OTHER PUBLICATIONS

International Preliminary Report on Patentability for the equivalent international patent application PCT/US2015/042572 dated Feb. 9, 2017.
S. Anirbid, et al., "Hydrocarbon reserve estimation using evolutionary programming technique," Current science, Jul. 10, 2003, vol. 85, No. 1, pp. 82-85.
Geoloil Corporation, "How to computer Petrophysical Cutoffs with GeolOil," Mar. 29, 2013, pp. 1-3.
Academic Center for Technology, "Net Pay Using Core Data," Oct. 12, 2013, pp. 1-22.
Extended Search Report for the equivalent European patent application 15826624.7 dated Mar. 19, 2018.

* cited by examiner

TOOL FOR CUTOFF VALUE DETERMINATION IN NET-PAY COMPUTATION WORKFLOW

CROSS-REFERENCE TO RELATED APPLICATIONS

This application claims priority to France National Patent Application Serial No. 1457311 filed on Jul. 29, 2014, which is incorporated by reference herein in its entirety.

BACKGROUND

Deciding whether to extract hydrocarbons from a hydrocarbon-bearing reservoir can be a complex task, particularly when the reservoir includes water saturation and porous lithology. Toward making such a decision, users may select water saturation and porosity cutoff values and use them to estimate a volume of economically available hydrocarbon. However, users have little guidance as to how such cutoff values may be selected.

SUMMARY

Embodiments of the present disclosure may include systems, methods, and computer-readable media for assessing porosity and water saturation cutoff values for available hydrocarbon volume estimation. The disclosed techniques can include obtaining, using an electronic processor, a plurality of water saturation and porosity value pairs for a plurality of locations in at least one borehole, and plotting, using an electronic processor, the plurality of water saturation and porosity value pairs on a graph, where the graph includes a water saturation axis and a porosity axis. The disclosed techniques can further include estimating, using an electronic processor and based on the plurality of water saturation and porosity value pairs, an estimated maximal hydrocarbon volume for the at least one borehole, and representing, using an electronic processor, a plurality of percentiles of the estimated maximal hydrocarbon volume on the graph. The disclosed techniques can also include causing, using an electronic processor, the graph to be displayed to a user, such that the user can visually observe a combined sensitivity to porosity and water saturation cutoffs values.

This summary is provided to introduce some of the subject matter described below and is not to be considered limiting.

BRIEF DESCRIPTION OF THE DRAWINGS

The accompanying drawings, which are incorporated in and constitute a part of this specification, illustrate embodiments of the present teachings and together with the description, serve to explain the principles of the present teachings. In the figures.

DETAILED DESCRIPTION

Figure 1:
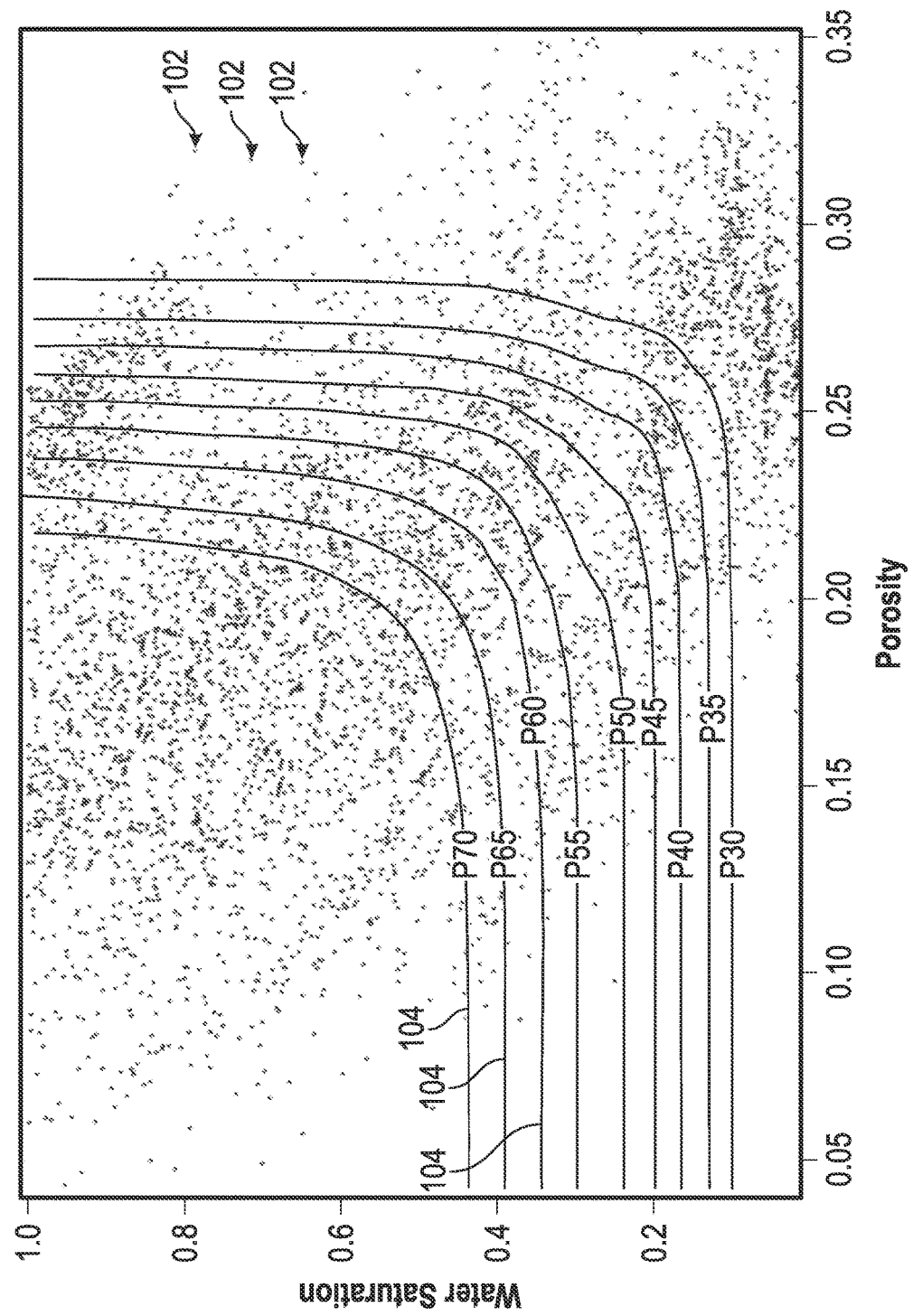
FIG. 1 is a plot of measured porosity and water saturation value pairs together with level curves representing various estimated maximal hydrocarbon volume percentiles according to various embodiments.

The following detailed description refers to the accompanying drawings. Wherever convenient, the same reference numbers are used in the drawings and the following description to refer to the same or similar parts. While several embodiments and features of the present disclosure are described herein, modifications, adaptations, and other implementations are possible, without departing from the spirit and scope of the present disclosure. Accordingly, the following detailed description does not limit the present disclosure. Instead, the proper scope of the disclosure is defined by the appended claims.

Making a decision as to whether to attempt to extract hydrocarbons from a reservoir may take many factors into account. One such factor is an estimation of available hydrocarbons in the reservoir. However, hydrocarbons within different rock formations in a reservoir may not be equally available. Porosity and water saturation are physical parameters that may be used to discriminate among rock formations holding hydrocarbons. For example, porous rock formations, rock formations that are water saturated, and rock formations that are both porous and at least partially water saturated, can contain hydrocarbons that are not economically viable for extraction, depending on the particular values of porosity and water saturation, among other factors. Moreover, a given reservoir can include both economically viable and economically prohibitive hydrocarbon deposits due to, among other factors, variations of porosity and water saturation of formations within the reservoir.

Estimating an available hydrocarbon volume for the reservoir can include guessing values for porosity and water saturation that encompass the actual values for the economically viable hydrocarbon deposits within the reservoir. That is, to estimate available hydrocarbons within a reservoir, some techniques attempt to partition formations within a reservoir into those that have suitable porosity and water saturation values, and those that do not. Such techniques then tally the hydrocarbons existing in economically viable deposits within the reservoir. To that end, such techniques can utilize estimated porosity and water saturation cutoff values, assuming for purposes of the calculation that the portions of the reservoir under analysis having porosity greater than the porosity cutoff value and having water saturation less than the water saturation cutoff value will produce hydrocarbons, and the other formations will not.

Selecting porosity and water saturation cutoff values for purposes of estimating available hydrocarbon volume in a reservoir can be complex. Some techniques for selecting porosity and water saturation cutoff values can rely solely on "gut intuition" of experienced personnel. In contrast, some embodiments provide analytic tools for selecting suitable cutoff values using objective parameters. One such parameter is how sensitive the estimated available hydrocarbon volume is to perturbations of both cutoff values. For example, if an estimated available hydrocarbon volume is highly sensitive to (i.e., highly variable as a function of) variations of a particular pair of cutoff values, then the estimate is entitled to low confidence. In contrast, if an estimated available hydrocarbon volume is relatively insensitive to variations of a particular pair of cutoff values, then a user may have a relatively higher confidence in the estimate.

Disclosed herein are computer-implemented techniques for assessing a joint sensitivity of estimated available hydrocarbon volume in a reservoir as affected by variations in porosity and water saturation cutoff values. The techniques can be used to select a particular pair of porosity and water saturation cutoff values reflecting a limited such joint sensitivity, and these values can be used to calculate an estimated available hydrocarbon volume. The estimated available hydrocarbon volume can in turn be used to, for example, assess whether a hydrocarbon-bearing reservoir is economically viable for extraction efforts, and physical extraction efforts can follow if so.

In sum, the techniques disclosed herein may be used to determine suitable porosity and water saturation cutoff values such that the resulting estimated available hydrocarbon volume has a relatively low combined sensitivity to perturbations of the underlying cutoff values. The selected values can be used to estimate an economically-available hydrocarbon volume in the reservoir, as well as a confidence in the estimation, and these factors can then be used as a basis for a decision as to whether to extract hydrocarbons from the reservoir.

FIG. 1 is a plot of measured porosity and water saturation value pairs together with level curves representing various estimated maximal hydrocarbon volume percentiles according to various embodiments. Plots such as the plot of FIG. 1 may be displayed according to various embodiments.

Each porosity and water saturation value pair illustrated on FIG. 1 as a dot 102 represents a pair of measured or derived values. In some embodiments, each pair of values represents parameters measured at regular intervals along the length of a borehole. For example, in some embodiments, each dot represents porosity and water saturation values at each 0.5 foot interval along the length of a borehole. In other embodiments, the intervals may be different, e.g., each four inches, each foot, etc. Values for porosity and water saturation may be measured using any known technique. Note that the specific values may be inferred or derived rather than measured directly. By way of non-limiting example, porosity may be derived, using known techniques, from sonic logs rather than by retrieving a rock sample and measuring average pore width, which may be impractical. Clusters of dots, should they occur, represent common porosity and water saturation values for the borehole. In some embodiments, the plotted dots represent measured values along the length of multiple boreholes accessing the same reservoir.

Also included in FIG. 1 are level curves 104 representing porosity and water saturation value pairs and corresponding to various percentiles of estimated maximal hydrocarbon volume. Toward determining an estimated maximal hydrocarbon volume, it is useful to first note that, in general, the relationship between porosity $\phi$ and water saturation sw for well data follows a hyperbolic form, which may be expressed as, by way of non-limiting example, Equation 1 below.

$$BVW = sw \cdot \phi \quad (1)$$

In Equation 1, BVW represents a fixed bulk volume of water, sw represents a water saturation value, and $\phi$ represents porosity. The relationship expressed by Equation (1) generally holds for a constant bulk volume of water for a given substrate grain size. Further, the bulk volume of water generally decreases with an increasing grain size. Thus, Equation (1) may be used to characterize the variation of pore geometry in a pool of well data under consideration.

Estimated maximal hydrocarbon volume, referred to as hydrocarbon pore volume, may be calculated using, by way of non-limiting example, Equation (2) below.

$$HCPV(\overline{x}) = \sum_{points\ of\ interest} h \cdot \phi \cdot (1 - sw) \quad (2)$$

In Equation (2), $HCPV(\overline{x})$ represents the hydrocarbon pore volume, measured linearly, calculated using the porosity cutoff $\phi_{cutoff}$ and water saturation cutoff $sw_{cutoff}$ value pair $\overline{x} = (\phi_{cutoff}, sw_{cutoff})$. The term h represents a thickness parameter, which can be, e.g., the sampling interval used to obtain the measured porosity and water saturation value pairs 102. The terms $\phi$ and sw represent the porosity and water saturation values, respectively, for the points of interest. The points of interest are the measured porosity and water saturation value pairs for which the porosity is greater than $\phi_{cutoff}$ and the water saturation is less than $sw_{cutoff}$.

Equation (2) may be used to calculate estimated maximal hydrocarbon volume by setting the porosity $\phi_{cutoff}$ to zero and the water saturation cutoff $sw_{cutoff}$ to 100%, i.e., maximal estimated hydrocarbon may be calculated as HCPC(0, 1) using Equation (2). The estimated hydrocarbon volume is "maximal" in the sense that it calculates a total amount of hydrocarbons that would be present if the portions capable of holding hydrocarbons are actually holding hydrocarbons.

Equation (2) can more generally be used to estimate an available hydrocarbon volume for any given pair of cutoff values $\overline{x} = (\phi_{cutoff}, sw_{cutoff})$. This reflects an understanding that some formations within the reservoir may not yield economically practicable hydrocarbons due to their unfavorable porosity and/or water saturation values.

Once an estimated maximal hydrocarbon volume is calculated for a given reservoir, level curves 104 of FIG. 1 may be plotted as follows. A given percentile of the estimated maximal hydrocarbon volume may be calculated as a product of estimated maximal hydrocarbon volume and the corresponding percentage. Each level curve 104 represents the porosity and water saturation cutoff values, any one of which, if used to calculate the estimated available hydrocarbon volume, e.g., using Equation (2), yields the specified percentile.

For example, if the maximal estimated maximal hydrocarbon volume is calculated as HCPC(0, 1)=1000 feet, the $70^{th}$ percentile would be 70% multiplied by 1000, or 700 feet. The $70^{th}$ percentile level curve 104 of FIG. 1 represents a set of cutoff values such that, if any one is used to determine an estimated available hydrocarbon volume, yield 700 feet. In other words, the $70^{th}$ percentile level curve 104 can be defined as the set of points ($\phi$, sw) such that HCPC($\phi$, sw)=700.

Thus, FIG. 1 shows a graph illustrating both measured porosity and water saturation values in a reservoir and estimated maximal hydrocarbon volume percentile level curves. A plot such as that depicted in FIG. 1 may be displayed according to some embodiments.

Figure 2:
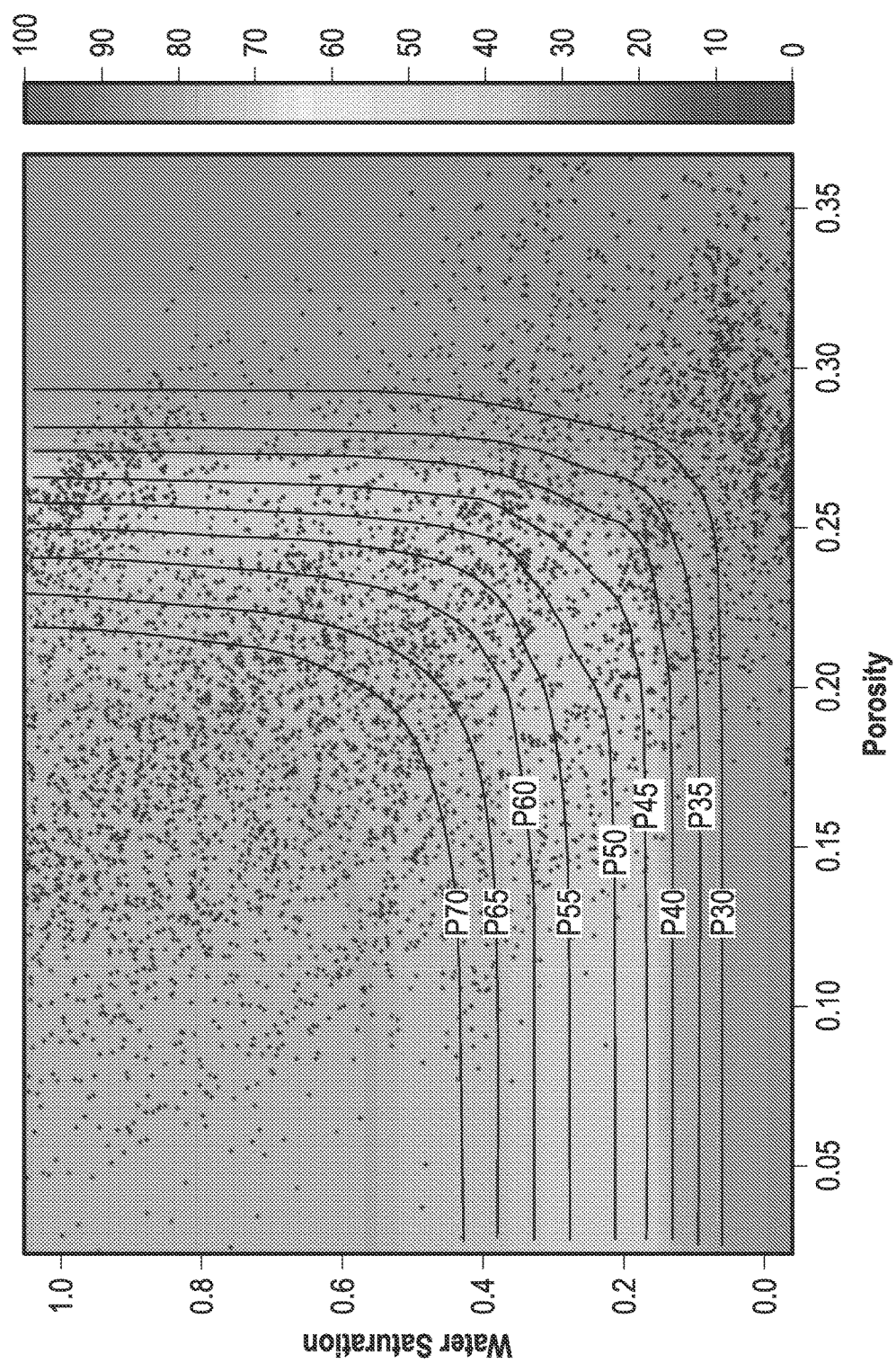
FIG. 2 is a plot of measured porosity and water saturation value pairs together with a heat map representing various estimated maximal hydrocarbon volume percentiles according to various embodiments.

FIG. 2 is a plot of measured porosity and water saturation value pairs together with a heat map representing various estimated maximal hydrocarbon volume percentiles according to various embodiments. Thus, FIG. 2 is similar to FIG.

1 in that they both include the same set of measured porosity and water saturation value pairs.

However, FIG. 2 differs from FIG. 1 in that FIG. 2 includes a heat map to represent estimated maximal hydrocarbon volume percentiles in addition to using level curves for the same purpose. As used herein, a "heat map" utilizes colors or shades to represent data values. The information needed to generate the plot of FIG. 2 is similar to that used to generate the plot of FIG. 2. For example, various percentiles of an estimated maximal hydrocarbon volume may be calculated as discussed above in reference to FIG. 1. The percentiles may be calculated at various intervals, e.g., each 5%: $5^{th}$, $10^{th}$, $15^{th}$, $20^{th}$, $25^{th}$, etc. Other intervals may be used in the alternative, e.g., 1%, 2%, 3%, 10%, etc. The percentiles of the estimated maximal hydrocarbon volume are plotted in FIG. 2 as a heat map using shades of grey. As depicted in FIG. 2, lower percentiles are generally darker, and higher percentiles are generally lighter. Other schemas for heat map presentation are also possible.

Figure 3:
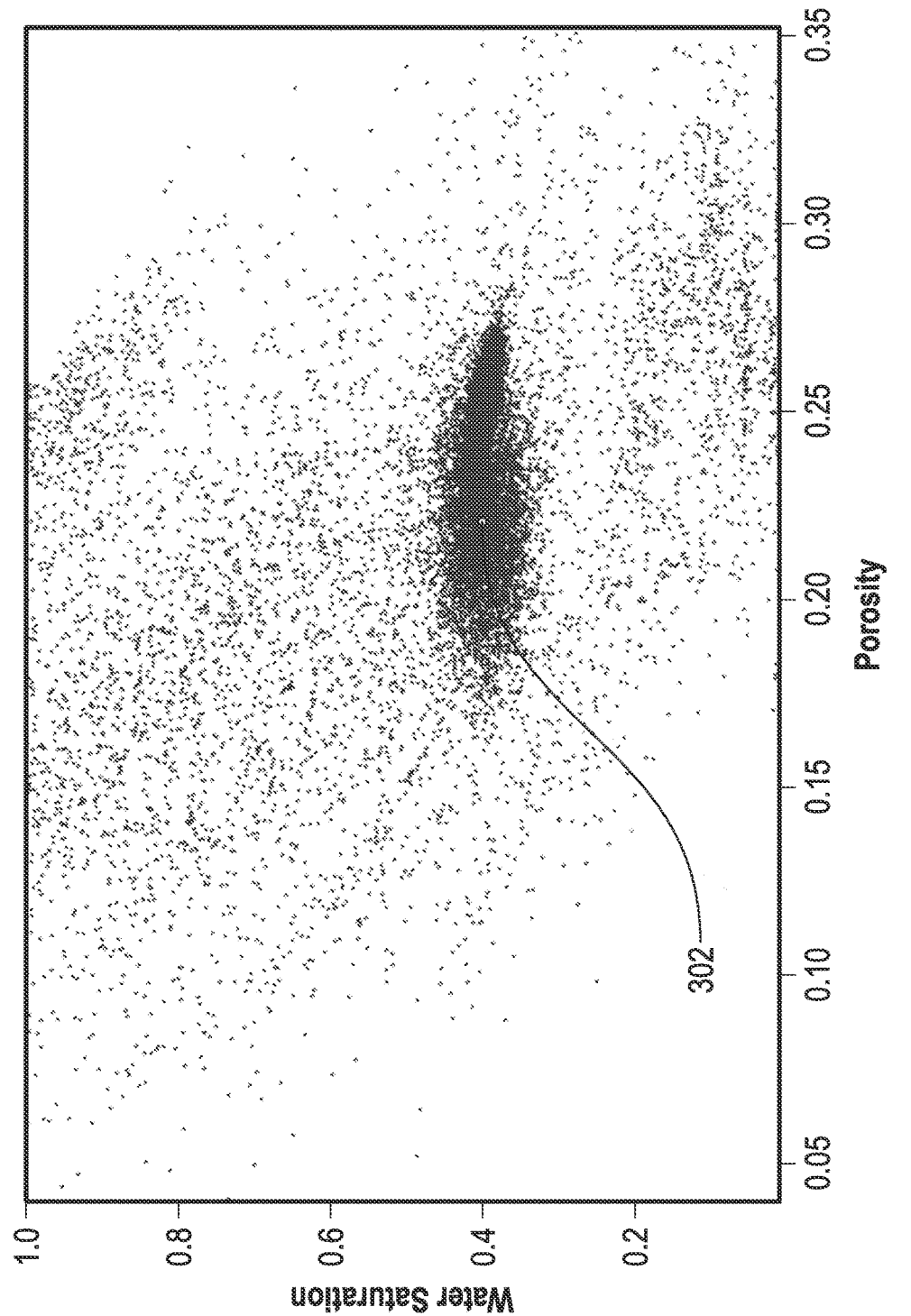
FIG. 3 is plot of measured porosity and water saturation value pairs according to various embodiments.

FIG. 3 is plot of measured porosity and water saturation value pairs according to various embodiments. A cluster of porosity and water saturation value pairs appears in the plot of FIG. 3 with point 302 at its center. The existence of the cluster indicates that many portions of the reservoir have similar values for porosity and water saturation. Faced with a decision as to whether to attempt hydrocarbon extraction from the reservoir, a user might select the values represented by point 302 as porosity and water saturation cutoff values, toward calculating a maximal available hydrocarbon volume. However, the plot of FIG. 3 tells very little about how sensitive the estimated available hydrocarbon volume is to the selected cutoff porosity and water saturation value pairs. As described below in reference to FIG. 4, point 302 might not be an optimal selection for cutoff values.

Figure 4:
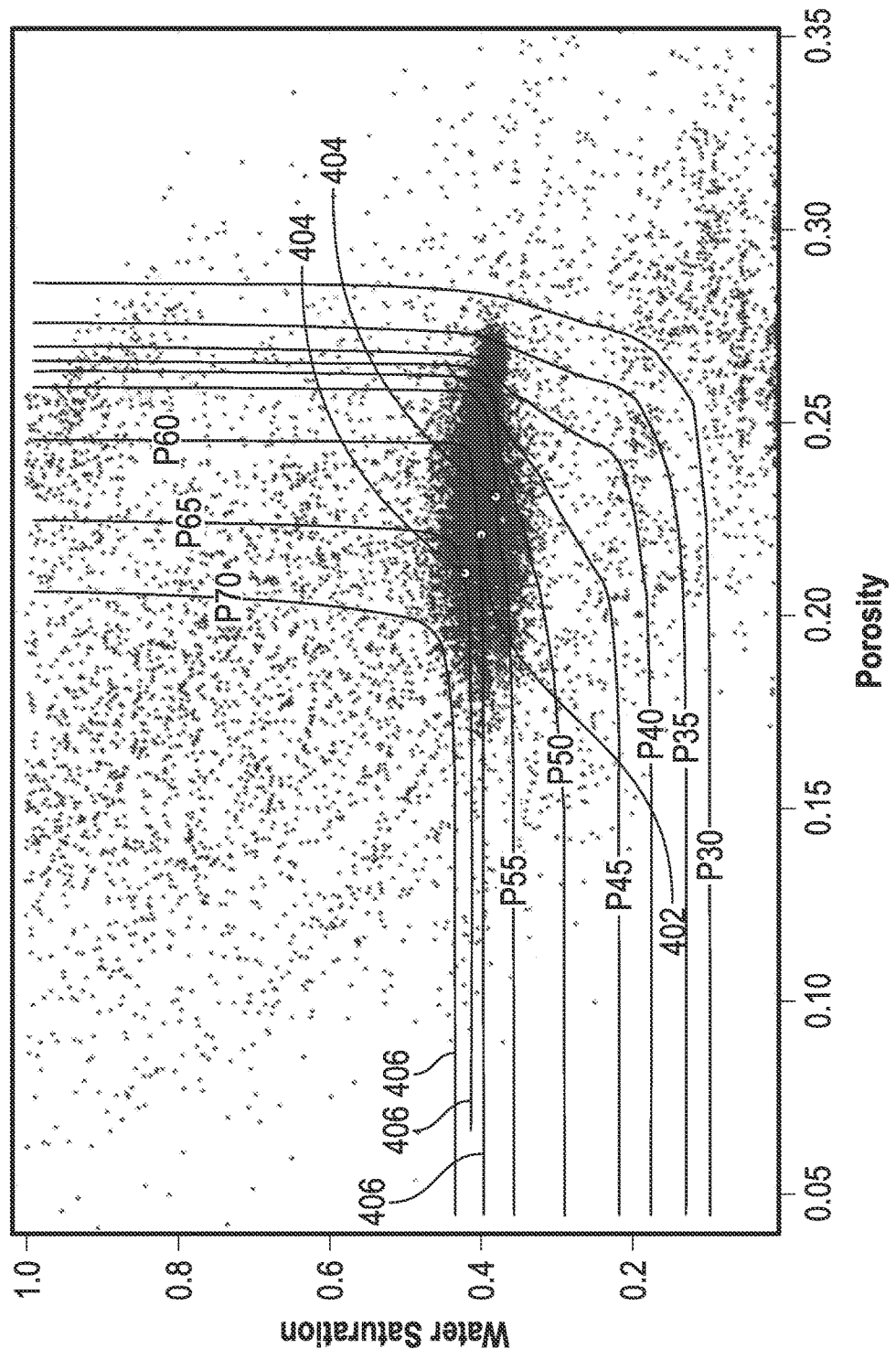
FIG. 4 is plot of measured porosity and water saturation value pairs together with level curves representing various estimated maximal hydrocarbon volume percentiles according to various embodiments.

FIG. 4 is plot of measured porosity and water saturation value pairs together with level curves representing various estimated maximal hydrocarbon volume percentiles according to various embodiments. In particular, the plot of FIG. 4 is the same as that of FIG. 3, except that the plot of FIG. 4 also includes level curves 406 representing various estimated maximal hydrocarbon volume percentiles.

Point 402, which corresponds to point 302 of FIG. 3, lies on the $60^{th}$ percentile level curve at roughly the center of the cluster of points. In addition, points 404 lie relatively close to point 402, but are on different level curves, namely, level curves representing the $55^{th}$ and $65^{th}$ percentiles. This indicates that an estimated available hydrocarbon volume calculated using point 402 as porosity and water saturation cutoff values would be relatively sensitive to perturbations in porosity and water saturation. It follows that an estimated available hydrocarbon volume calculated using point 402 as porosity and water saturation cutoff values would not be entitled to a high degree of confidence. Plotting level curves 406 together with the points makes it easier to assess the sensitivity of an estimated available hydrocarbon volume to perturbations in porosity and water saturation. In general, the narrower the spacing between level curves (or the closer together the colors are on a heat map version), the lower the confidence in an associated estimate.

Figure 5:
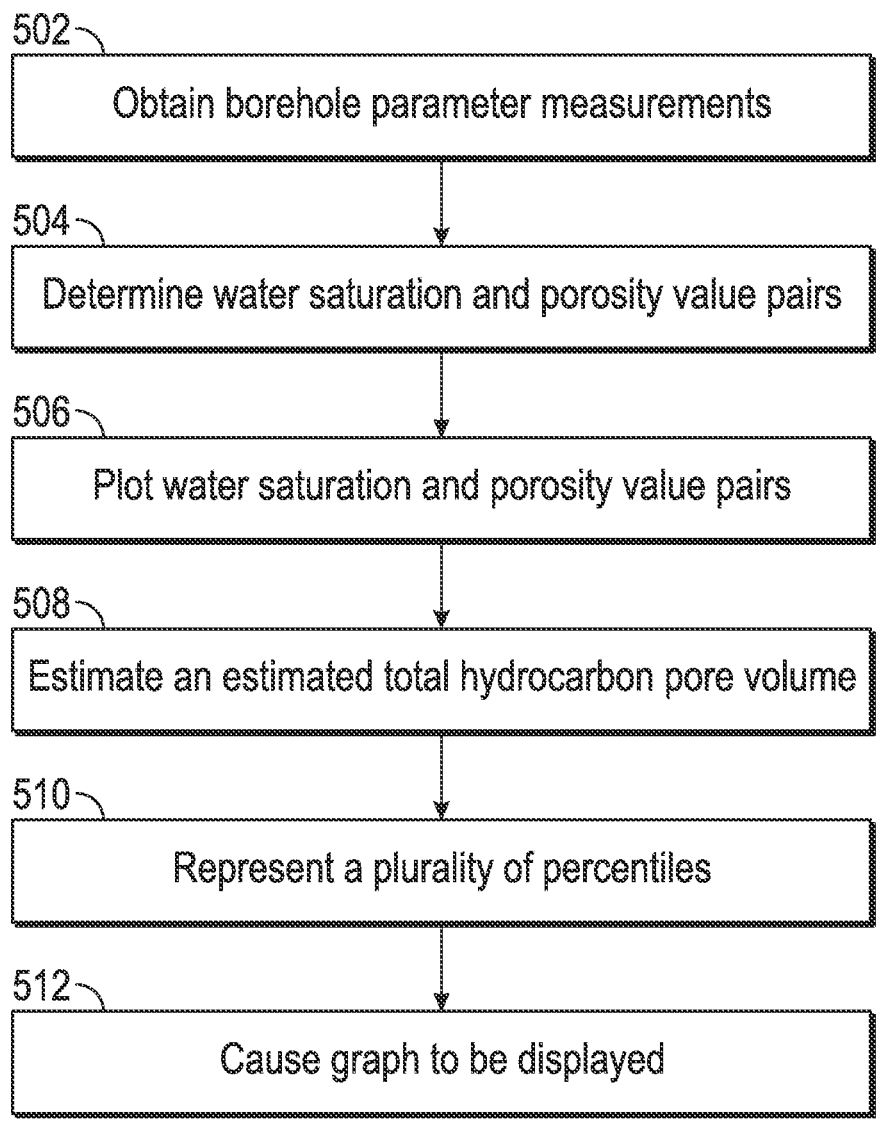
FIG. 5 is a flowchart depicting a method according to various embodiments.

FIG. 5 is a flowchart depicting a method according to various embodiments. The method of FIG. 5 may be at least partially implemented on an electronic computer.

At block 502, the method obtains borehole parameter measurements. The measurements may be made at regular intervals (e.g., 2 inches, 4 inches, 6 inches, 8 inches, 10 inches, foot, etc.) along the length of one or more boreholes associated with a reservoir. Such measurements may be of any parameter or parameters from which porosity and/or water saturation values may be derived using known techniques. Example parameters and techniques for the measuring of block 502 include, by way of non-limiting example: sonic readings, radiological measurements, electrical resistivity, depth, spin echo magnetic resonance, nuclear magnetic resonance, hydrogen index, gamma logs, etc. Block 502 may obtain such measurements by inputting data into a programmed electronic computer, for example. Other techniques include receiving over a network, accessing persistently stored data, etc.

At block 504, the method determines porosity and water saturation values from the data obtained at block 502. The specific determinations performed at block 504 are dependent on the types of data obtained at block 502. That is, the method uses known techniques to derive porosity and water saturation values corresponding to the data obtained at block 502. The determinations may be performed automatically by a programmed computer. The result of block 504 is an electronically-accessible set of porosity and water saturation values for multiple locations in the associated borehole(s). The values may be stored in persistent memory.

At block 506, the method plots the water saturation and porosity value pairs. The resulting plot may be of the form presented in any of FIGS. 1-4 with respect to the porosity and water saturation value pairs. The plotting may be accomplished electronically by a programmed computer. The plotting may be performed by generating and storing a data structure representing the plot and including points representing the porosity and water saturation value pairs determined at block 504. The data structure may be in any of a variety of formats including, by way of non-limiting example, JPEG, GIF, bitmap, etc.

At block 508, the method estimates an estimated maximal hydrocarbon volume. The estimation may be based on the porosity and water saturation value pairs determined at block 504 and calculated using Equation (2) as described above. The calculation may be performed by a programmed computer. The result of the calculation may be stored in persistent memory, for example.

At block 510, the method represents a plurality of percentiles of the estimated maximal hydrocarbon volume calculated at block 508. The representation may include plotting level curves or a heat map as discussed extensively herein. A user may utilize a user interface (discussed further below) to select level curves, a heat map, or both, to represent the percentiles. The plotting may be accomplished by a programmed computer. The plotting may be performed by modifying the data structure generated at block 506, for example, to include level curves and/or a heat map representation. The modified data structure may be stored in persistent memory, for example.

At block 512, the method causes the resulting graph to be displayed. The graphs may appear as the plots illustrated in any of FIGS. 1, 2, and 4. Block 512 may be performed by a programed electronic computer. The displaying may be accomplished by programming the computer to cause a video interface to generate a signal interpretable by an electronic display, where the signal represents at least the plot generated and stored according to the preceding blocks. That is, the displaying may be accomplished by causing an electronic computer to display the plot.

In general, some embodiments include a user interface through which the user may customize the plot and/or display. For example, a user can select whether to display estimated maximal hydrocarbon volume percentiles as level curves, as a heat map, or both. The user can select which, how many, and at what intervals, percentiles may be represented, particularly for percentiles represented by level curves.

Some embodiments provide a user with a user-controlled pointer with special abilities to interact with the displayed plot. The pointer may appear as a cross controlled by the user using a mouse, for example. The user moving the pointer to a given cutoff pair may allow the user to visualize the points selected for computation of an estimated available hydrocarbon volume, e.g., points with porosity values greater than the porosity cutoff value and with water saturation values less than the water saturation cutoff value. The values for the cutoffs pair may be displayed near the cross, as well as the value of the estimated available hydrocarbon volume for the cutoffs. Default cutoff values or cutoff values typed by the user in the user interface may be automatically displayed on the plot, with a pointer at the selected cutoffs pair. When the user moves the pointer, the values of the cutoffs in the interface may automatically update accordingly. When the user moves the mouse along the percentile level curves, for example, the values for the cutoffs pair on the curve may be displayed, as well as the value of the estimated available hydrocarbon volume for these cutoffs.

Various embodiments can be used in a variety of ways for a variety of purposes. An example use case includes assisting in selecting cutoff values. More particularly, some embodiments can assist a user by helping to visualize sensitivity to cutoff values of an estimated available hydrocarbon volume. Some embodiments can be used to observe the sensitivity of the estimated available hydrocarbon volume to the combined choice of both cutoff values. Alternately, or in addition, some embodiments can help a user to visualize the sensitivity to each cutoff individually, along each axis.

Further, some embodiments can assist a user in choosing a range of porosity and water saturation cutoff values. This way, the user can obtain pessimistic to optimistic estimations of available hydrocarbon volume. Using the displayed levels, the user can choose to perform an available hydrocarbon volume estimation computation for the cutoff values in a range delimited by, e.g., the $10^{th}$ and $90^{th}$ percentiles.

Yet further, some embodiments assist a user in assessing the user's choice for cutoff values. Variations of estimated available hydrocarbon volume for small variations in the cutoffs around the chosen values can be observed. This way, some embodiments help assess confidence in the estimation of available hydrocarbon volume for the chosen cutoff values. If local sensitivity is low, confidence in the estimated available hydrocarbon volume is high with respect to the cutoff values.

Variations in embodiments are also contemplated. One such variation includes computing lithology values for the well, so that each well data at a given depth is associated with a rock type in addition to a porosity and a water saturation. In such embodiments, well data with oil-bearing lithology are used in the calculation for estimation of available hydrocarbon volume for a given pair of cutoff values. In such embodiments, the set points of interest as used in Equation (2) may be thinned such that values associated with oil-bearing lithology are used for the computation.

Another variation includes accounting for depth. That is, in some embodiments, the computation of estimated available hydrocarbon volume takes depth into account. For a given pair of porosity and water saturation cutoff values, a set of points of interests may be selected for computation. From these points, points that are isolated along the well, or building a thin layer below some thickness threshold, may be discarded. This refinement computes hydrocarbon volume estimated with an algorithm that performs thin bed removal.

Figure 6:
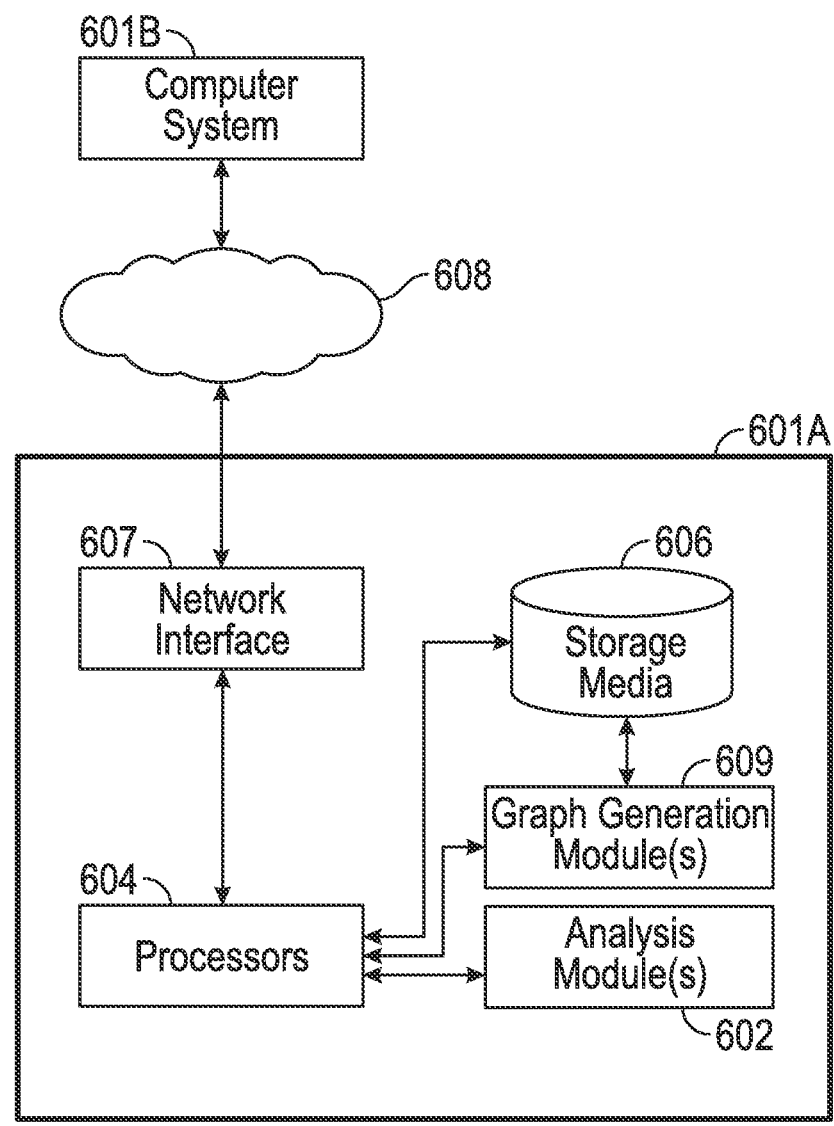
FIG. 6 illustrates an example computing system in accordance with some embodiments.

FIG. 6 illustrates an example computing system 601A in accordance with some embodiments. The computing system 601A can be an individual computer system or an arrangement of distributed computer systems. The computing system 601A includes one or more analysis modules 602 that are configured to perform various tasks according to some embodiments, such as one or more methods disclosed herein (e.g., the method of FIG. 5). To perform these various tasks, analysis module 602 executes independently, or in coordination with, one or more processors 604, which is (or are) connected to one or more storage media 606. The processor(s) 604 is (or are) also connected to a network interface 607 to allow the computer system 601A to communicate over a data network 608 with one or more additional computer systems and/or computing systems, such as 601B (note that computer system 601B may or may not share the same architecture as computer system 601A, and may be located in different physical locations, e.g., computer system 601A may be in a laboratory, while in communication with one or more computer systems such as 601B, located in one or more data centers or reservoir sites, and/or located in varying countries on different continents). The processor(s) 604 can include a microprocessor, microcontroller, processor module or subsystem, programmable integrated circuit, programmable gate array, or another control or computing device.

The storage media 606 can be implemented as one or more computer-readable or machine-readable storage media. Note that while in the example embodiment of FIG. 6, storage media 606 is depicted as within computer system 601A, in some embodiments, storage media 606 may be distributed within and/or across multiple internal and/or external enclosures of computing system 601A and/or additional computing systems. Storage media 606 may include one or more different forms of memory including semiconductor memory devices such as dynamic or static random access memories (DRAMs or SRAMs), erasable and programmable read-only memories (EPROMs), electrically erasable and programmable read-only memories (EEPROMs) and flash memories, magnetic disks such as fixed, floppy and removable disks, other magnetic media including tape, optical media such as compact disks (CDs) or digital video disks (DVDs), BluRays, or other types of optical storage, or other types of storage devices. Note that the instructions discussed above can be provided on one computer-readable or machine-readable storage medium, or alternatively, can be provided on multiple computer-readable or machine-readable storage media distributed in a large system having possibly plural nodes. Such computer-readable or machine-readable storage medium or media is (are) considered to be part of an article (or article of manufacture). An article or article of manufacture can refer to any manufactured single component or multiple components. The storage medium or media can be located either in the machine running the machine-readable instructions, or located at a remote site from which machine-readable instructions can be downloaded over a network for execution.

In some embodiments, computing system 601A contains one or more graph generation module(s) 609. In the example of computing system 601A, computer system 601A includes graph generation module 609. In some embodiments, a single graph generation module working on concert with the rest of computing system 601A may be used to perform some or all aspects of the method of FIG. 5.

It should be appreciated that computing system 601A is one example of a computing system, and that computing system 601A may have more or fewer components than shown, may combine additional components not depicted in the example embodiment of FIG. 6, and/or computing system 600A may have a different configuration or arrangement of the components depicted in FIG. 6. The various components shown in FIG. 6 may be implemented in hardware, software, or a combination of both hardware and software, including one or more signal processing and/or application specific integrated circuits.

Further, the steps in the processing methods described herein may be implemented by running one or more functional modules in information processing apparatus such as general purpose processors or application specific chips, such as ASICs, FPGAs, PLDs, or other appropriate devices. These modules, combinations of these modules, and/or their combination with general hardware are included within the scope of protection of embodiments of the invention.

The steps described herein need not be performed in the same sequence discussed or with the same degree of separation. Various steps may be omitted, repeated, combined, or divided, to achieve the same or similar objectives or enhancements. Accordingly, the present disclosure is not limited to the above-described embodiments, but instead is defined by the appended claims in light of their full scope of equivalents.

What is claimed is:

1. A computer implemented method for assessing porosity and water saturation cutoff values for hydrocarbon volume estimation, the method comprising:
    obtaining a plurality of water saturation and porosity value pairs for a plurality of locations in at least one borehole;
    plotting the plurality of water saturation and porosity value pairs on a graph, wherein the graph comprises a water saturation axis and a porosity axis;
    estimating, based on the plurality of water saturation and porosity value pairs, an estimated maximal hydrocarbon volume for the at least one borehole;
    representing a plurality of percentiles of the estimated maximal hydrocarbon volume on the graph; and
    causing the graph to display a combined sensitivity to porosity and water saturation cutoffs values.

2. The method of claim 1, further comprising:
    selecting a selected porosity cutoff value and a selected water saturation cutoff value;
    determining an estimated available hydrocarbon volume for the selected porosity cutoff value and the selected water saturation cutoff value;
    deciding, based on the estimated available hydrocarbon volume and on the combined sensitivity, to extract at least some hydrocarbon from the borehole; and
    extracting, based on the estimated available hydrocarbon volume and on the combined sensitivity, at least some hydrocarbon from the borehole.

3. The method of claim 1, wherein the estimating the estimated maximal hydrocarbon volume comprises computing a sum of products, wherein each product comprises a porosity value and a non-water saturation value.

4. The method of claim 3, wherein the sum ranges over a subset of the plurality of water saturation and porosity value pairs.

5. The method of claim 4, wherein the subset excludes at least one water saturation and porosity value pair associated with a non-hydrocarbon-bearing lithology.

6. The method of claim 1 further comprising providing for display a water saturation value associated with a position of a user-controlled pointer, a porosity value associated with the position of the pointer, and an estimated available hydrocarbon volume associated with the position of the pointer.

7. The method of claim 6, wherein the providing for display comprises providing for dynamic display a fixed distance from the pointer.

8. The method of claim 6,
    wherein the estimated available hydrocarbon volume is calculated as a sum of products,
    wherein each product comprises a porosity value and a non-water saturation value,
    wherein the sum ranges over a subset of the plurality of water saturation and porosity value pairs, and
    wherein the subset excludes water saturation and porosity value pairs that include a porosity value less than a value associated with a position of the pointer, a water saturation value greater than a water saturation value associated with a position of the pointer, or both.

9. The method of claim 1, wherein the representing comprises representing as a heat map.

10. The method of claim 1, wherein the representing comprises representing as a plurality of level curves.

11. A computing system, comprising:
    one or more processors;
    at least one memory; and
    one or more programs stored in the at least one memory, wherein the one or more programs are configured to be executed by the one or more processors, the one or more programs including instructions for:
    obtaining a plurality of water saturation and porosity value pairs for a plurality of locations in at least one borehole;
    plotting the plurality of water saturation and porosity value pairs on a graph, wherein the graph comprises a water saturation axis and a porosity axis;
    estimating, based on the plurality of water saturation and porosity value pairs, an estimated maximal hydrocarbon volume for the at least one borehole;
    representing a plurality of percentiles of the estimated maximal hydrocarbon volume on the graph; and
    causing the graph to display a combined sensitivity to porosity and water saturation cutoffs values.

12. The system of claim 11, wherein the one or more programs further include instructions for:
    selecting a selected porosity cutoff value and a selected water saturation cutoff value;
    determining an estimated available hydrocarbon volume for the selected porosity cutoff value and the selected water saturation cutoff value;
    deciding, based on the estimated available hydrocarbon volume and on the combined sensitivity, to extract at least some hydrocarbon from the borehole; and
    extracting, based on the estimated available hydrocarbon volume and on the combined sensitivity, at least some hydrocarbon from the borehole.

13. The system of claim 11, wherein the estimating the estimated maximal hydrocarbon volume comprises computing a sum of products, wherein each product comprises a porosity value and a non-water saturation value.

14. The system of claim 13, wherein the sum ranges over a subset of the plurality of water saturation and porosity value pairs.

15. The system of claim 14, wherein the subset excludes at least one water saturation and porosity value pair associated with a non-hydrocarbon-bearing lithology.

16. The system of claim 11, wherein the one or more programs further include instructions for: providing for display a water saturation value associated with a position of a user-controlled pointer, a porosity value associated with the position of the pointer, and an estimated available hydrocarbon volume associated with the position of the pointer.

17. The system of claim 16, wherein the providing for display comprises providing for dynamic display a fixed distance from the pointer.

18. The system of claim 16,
wherein the estimated available hydrocarbon volume is calculated as a sum of products,
wherein each product comprises a porosity value and a non-water saturation value,
wherein the sum ranges over a subset of the plurality of water saturation and porosity value pairs, and
wherein the subset excludes water saturation and porosity value pairs that include a porosity value less than a value associated with a position of the pointer, a water saturation value greater than a water saturation value associated with a position of the pointer, or both.

19. The system of claim 11, wherein the representing comprises representing as a heat map.

20. The system of claim 11, wherein the representing comprises representing as a plurality of level curves.

* * * * *